US012565677B2

(12) United States Patent
Liao et al.

(10) Patent No.: US 12,565,677 B2
(45) Date of Patent: Mar. 3, 2026

(54) SINGLE-CHANNEL SEQUENCING METHOD BASED ON SELF-LUMINESCENCE

(71) Applicant: Qingdao MGI Tech Co., Ltd., Qingdao (CN)

(72) Inventors: Sha Liao, Shenzhen (CN); Xi Chen, Shenzhen (CN); Ao Chen, Shenzhen (CN); Wenwei Zhang, Shenzhen (CN); Chongjun Xu, Shenzhen (CN); Hongmin Chen, Shenzhen (CN); Jie Zhao, Shenzhen (CN); Defeng Fu, Shenzhen (CN)

(73) Assignee: QINGDAO MGI TECH CO., LTD., Qingdao (CN)

(*) Notice: Subject to any disclaimer, the term of this patent is extended or adjusted under 35 U.S.C. 154(b) by 1071 days.

(21) Appl. No.: 17/608,316

(22) PCT Filed: May 15, 2019

(86) PCT No.: PCT/CN2019/086974

§ 371 (c)(1),
(2) Date: Nov. 2, 2021

(87) PCT Pub. No.: WO2020/227953

PCT Pub. Date: Nov. 19, 2020

(65) Prior Publication Data

US 2022/0205036 A1 Jun. 30, 2022

(51) Int. Cl.

*C12Q 1/68* (2018.01)
*C12Q 1/6853* (2018.01)
*C12Q 1/6869* (2018.01)

(52) U.S. Cl.

CPC ......... *C12Q 1/6869* (2013.01); *C12Q 1/6853* (2013.01)

(58) Field of Classification Search

CPC ............................ C12Q 1/6869; C12Q 1/6853
See application file for complete search history.

(56) References Cited

U.S. PATENT DOCUMENTS

| | | | |
|---|---|---|---|
| 2013/0079232 | A1 | 3/2013 | Kain et al. |
| 2019/0330693 | A1 | 10/2019 | Liu et al. |

FOREIGN PATENT DOCUMENTS

| | | | |
|---|---|---|---|
| CA | 3049667 | A1 | 7/2018 |
| CN | 1854308 | A | 11/2006 |
| CN | 108697499 | A | 10/2018 |
| WO | 2016040607 | A1 | 3/2016 |
| WO | 2018121587 | A1 | 7/2018 |
| WO | 2018129214 | A1 | 7/2018 |
| WO | 2018165099 | A1 | 9/2018 |

OTHER PUBLICATIONS

Application No. EP19928475.3, Extended European Search Report, Mailed on Dec. 22, 2022, 10 pages.
Japanese Application No. 2021-563644, Office Action mailed on Jun. 20, 2023, 9 pages (5 pages of Original Document and 4 pages of English Translation).
International Application No. PCT/CN2019/086974, International Preliminary Report on Patentability mailed on Nov. 25, 2021, 5 pages.
Singaporean Application No. 11202111778Y, Written Opinion mailed on Sep. 18, 2023, 10 pages.
PCT/CN2019/086974, "International Search Report, translation and Written Opinion", Nov. 19, 2020, 8 pages.
Jia Guo et al., Four-color DNA sequencing with 3'-O-modified nucleotide reversible terminators and chemically cleavable fluorescent dideoxynucleotides, Proc Natl Acad Sci, 105(27): 9145-9150, 2008.
Examination Report issued in Indian corresponding application No. 202117057104 mailed on Jan. 7, 2026, 7 pages.

*Primary Examiner* — Jezia Riley
(74) *Attorney, Agent, or Firm* — Kilpatrick Townsend & Stockton LLP; Yifan Mao

(57) ABSTRACT

The present invention provides a sequencing method based on a single fluorescent dye, in which a self-luminescence signal is used to distinguish the sequential incorporation of different nucleotides, thereby realizing the determination of the polynucleotide sequence.

13 Claims, 1 Drawing Sheet

Specification includes a Sequence Listing.

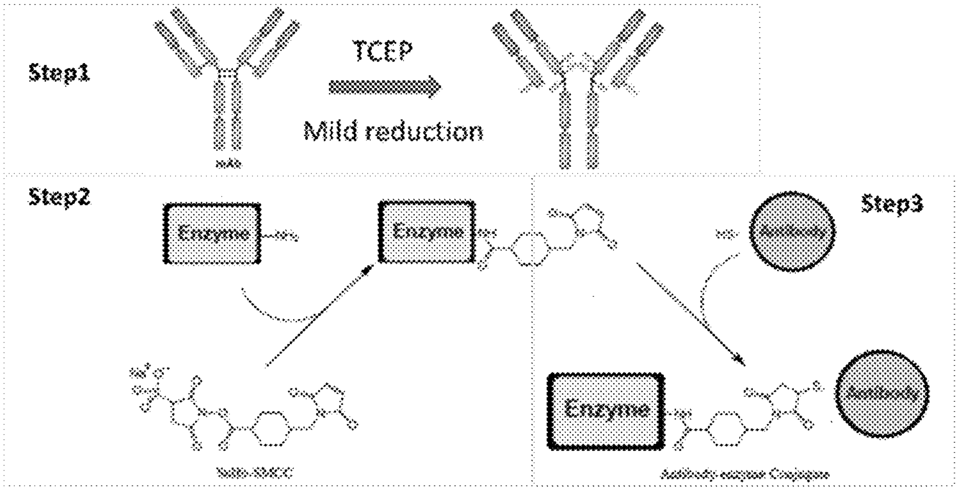
Step1
TCEP
Mild reduction
Step2
Enzyme
Enzyme
Step3
Enzyme

SINGLE-CHANNEL SEQUENCING METHOD BASED ON SELF-LUMINESCENCE

CROSS-REFERENCE TO RELATED APPLICATIONS

This application claims benefit and is a 371 application of PCT Application No. PCT/CN2019/086974, filed May 15, 2019, the entire contents of which is incorporated herein by reference for all purposes.

SEQUENCE LISTING

The instant application contains a Sequence Listing which has been submitted electronically in ASCII format and is hereby incorporated by reference in its entirety. Said ASCII copy, created on Oct. 15, 2021, is named IEC190036PCT_Sequence_Listing.txt and is 2 KB in size.

TECHNICAL FIELD

The present invention relates to the field of nucleic acid sequencing. In particular, the present invention provides a self-luminescence-based single-channel sequencing method, in which the self-luminescence signal is used to distinguish the sequential incorporation of different nucleotides, thereby realizing the determination of polynucleotide sequence.

BACKGROUND

DNA sequencing technology includes the first-generation DNA sequencing technology represented by Sanger sequencing method and the second-generation DNA sequencing technology represented by Illumina Hiseq2500, Roche 454, ABI Solid, BGISEQ-500, etc. In 1977, Sanger invented the dideoxy terminal termination sequencing method and became the representative of the first-generation of sequencing technology. In 2001, relying on the first-generation of sequencing technology, the human genome draft was completed. Sanger sequencing has the characteristics of simple experimental operation, intuitive and accurate results, and short experimental period. It has a wide range of applications in clinical gene mutation detection and genotyping that require high timeliness of detection results. However, the shortcomings of Sanger sequencing method are low throughput and high cost, which limits its application in large-scale gene sequencing. In order to overcome the shortcomings of Sanger sequencing method, the second-generation sequencing technology came into being. Compared with the first-generation DNA sequencing technology, the second-generation DNA sequencing technology has the characteristics of high sequencing throughput, low cost, high degree of automation, and single-molecule sequencing. Taking the sequencing technology of Hiseq2500V2 as an example, one experimental process can generate data of 10 to 200G bases, and the average sequencing cost per base is less than 1/1000 of the sequencing cost of Sanger sequencing method, and the sequencing results obtained can be processed and analyzed directly by the computer. Therefore, the second-generation DNA sequencing technology is very suitable for large-scale sequencing.

The second-generation DNA sequencing technologies that have been developed currently mainly involve sequencing by ligation (SBL) technology and sequencing by synthesis (SBS) technology. Typical examples of these sequencing technologies include the SOLiD sequencing method developed by Applied Biosystems, the combined probe anchor ligation (cPAL) method independently developed by Complete Genomics and the combined probe anchor synthesis (cPAS) method developed by the Beijing Genomics Institute (BGI), the Illumina sequencing method developed jointly by Illumina Company and Solexa Technology Company, etc. In these sequencing methods, Illumina and Complate Genomics adopt the method of detecting light signals, and in order to realize the identification and differentiation of 4 kinds of bases (A, T/U, C and G), it is usually necessary to use 4 kinds of fluorescent dyes to respectively label these 4 bases. In this case, in order to read the fluorescent signal carried by each base, the sequencing device must be equipped with at least two monochromatic excitation light sources and at least two cameras, which results in expensive manufacturing cost and huge volume of the sequencing device.

In the past 10 years, the second-generation gene sequencing technologies have gradually grown from emerging technologies to mainstream sequencing methods, and have gradually become important testing tools in the clinical field, thereby playing an increasing role in the prevention and control of infectious diseases, the diagnosis of genetic diseases, and non-invasive prenatal screening. In order to further expand the sequencing market and make sequencers popular, the development of low-cost and miniaturized sequencers has gradually become a development trend in the sequencing field. As a classic method of second-generation sequencing technology, the three sequencing methods based on four-channel, dual-channel and single-channel have their own advantages; in their comparison, the single-channel sequencing has advantages of less consumables, lower costs, easier to achieve miniaturization and portable instrumentation, and gradually becomes the development trend in the sequencing field. Currently, products based on monochrome channel on the market mainly include ion torrent series sequencers, 454 sequencers and the latest Iseq100 from Illumina.

Among the current sequencing technologies based on single-channel, the ion torrent series of instruments have limited their use due to the high error rate of polymer structure sequencing. Similarly, Roche's 454 instrument is also gradually withdrawn from the sequencing market due to insufficient sequencing accuracy and high sequencing cost. Illumina's Iseq100 is based on monochromatic fluorescence technology and semiconductor technology to realize the miniaturization of sequencer and maintain high sequencing quality. However, because the optical signal is excited by laser, the instrument is equipped with an additional laser, which increases the volume of the instrument. In addition, in order to avoid the background value generated by the excitation light, special processing must be performed on the semiconductor chip to filter out the background generated by the excitation light, and this processing will cause high costs and increased sequencing costs.

Therefore, there is a need in the art for a low-cost sequencing method that does not require external light source excitation and does not need to adopt an additional design to filter the background generated by laser light source.

SUMMARY

In order to solve the above-mentioned technical problems, the inventor of the present application has developed a new sequencing method that uses a signal of a self-luminescence system to distinguish four bases of A, (T/U), C and G.

Therefore, the luminescence signal used to implement the sequencing method of the present invention is derived from bioluminescence or chemiluminescence, so there is no need to configure an additional laser, and there is no need to adopt an additional design to filter the background generated by laser light source, which reduces the sequencing cost. The sequencing device used in the sequencing method of the present invention can even be conveniently carried around for immediate/on-site detection. In addition, the 3'-terminal hydroxyl of deoxyribonucleotide used in the sequencing method of the present invention is modified and blocked. During the sequencing process, only one deoxyribonucleotide can be synthesized in each reaction, ensuring that only one deoxyribonucleotide is bound in each reaction, thereby improving the accuracy of sequencing.

In one aspect, the present invention provides a method for sequencing a nucleic acid molecule, which comprises the following steps:

(1) providing a nucleic acid molecule to be sequenced that is linked to a support, or linking a nucleic acid molecule to be sequenced to a support;

(2) adding a primer for initiating a nucleotide polymerization reaction, a polymerase for performing the nucleotide polymerization reaction, and four compounds to form a reaction system containing a solution phase and a solid phase; wherein, the four compounds are respectively derivatives of nucleotides A, (T/U), C and G, and have the ability of base complementary pairing; and, the hydroxyl (—OH) at the 3'-position of ribose or deoxyribose of the four compounds is protected by a protecting group; and, the first compound is linked with a first molecular label, the second compound is linked with a second molecular label, the third compound is linked with a first molecular label and a second molecular label, or a part of the third compound is linked with a first molecular label and another part of the third compound is linked with a second molecular label, the fourth compound is not linked with any molecular label;

(3) annealing the primer to the nucleic acid molecule to be sequenced, and forming a duplex linked to the support by using the primer as an initial growing nucleic acid chain together with the nucleic acid molecule to be sequenced;

(4) using the polymerase to carry out the nucleotide polymerization reaction under a condition that allows the polymerase to carry out the nucleotide polymerization reaction, thereby incorporating one of the four compounds into the 3'-end of the growing nucleic acid chain;

(5) allowing the duplex of the previous step to contact with two different luciferases and perform a ligation reaction, wherein the two luciferases can specifically be ligated with the first molecular label and the second molecular label, respectively; then, allowing the luciferases to undergo a fluorescence reaction in the presence of a substrate, and detecting an emitted fluorescence signal;

(6) removing the molecular label of each nucleotide;

(7) optionally, repeating steps (3) to (7) to obtain sequence information of the nucleic acid molecule.

In an embodiment of the present invention, the self-luminescence detection of the nucleotide to be sequenced is realized through the ligation of luciferase and nucleotide derivative, so that no additional excitation light source is needed. In a specific embodiment, the ligation of luciferase and the nucleotide is achieved through the specific binding of the label on the luciferase and the corresponding label on the nucleotide derivative. In a specific embodiment, the first nucleotide is ligated with a first luciferase, the second nucleotide is ligated with a second luciferase, the third nucleotide is ligated with a first luciferase and a second luciferase, and the fourth nucleotide is not ligated with any luciferase. Then, the luminescence signals of the four bases are detected by passing the corresponding substrates of the two luciferases; when the substrate of the first luciferase is passed, the first and third nucleotides emit light, when the substrate of the second luciferase is passed, the second and third nucleotides emit light, so the bases can be identified according to the luminescence of the four nucleotides.

Therefore, in an exemplary embodiment, the method for sequencing a nucleic acid molecule of the present invention comprises the following steps:

(1) providing a nucleic acid molecule to be sequenced that is linked to a support, or linking a nucleic acid molecule to be sequenced to a support;

(2) adding a primer for initiating a nucleotide polymerization reaction, a polymerase for performing the nucleotide polymerization reaction, and four compounds to form a reaction system containing a solution phase and a solid phase; wherein, the four compounds are respectively derivatives of nucleotides A, (T/U), C and G, and have the ability of base complementary pairing; and, the hydroxyl (—OH) at the 3'-position of ribose or deoxyribose of the four compounds is protected by a protecting group; and, the first compound is linked with a first molecular label, the second compound is linked with a second molecular label, the third compound is linked with a first molecular label and a second molecular label, or a part of the third compound is linked with a first molecular label and another part of the third compound is linked with a second molecular label, the fourth compound is not linked with any molecular label;

(3) annealing the primer to the nucleic acid molecule to be sequenced, and forming a duplex linked to the support by using the primer as an initial growing nucleic acid chain together with the nucleic acid molecule to be sequenced;

(4) using the polymerase to carry out the nucleotide polymerization reaction under a condition that allows the polymerase to carry out the nucleotide polymerization reaction, thereby incorporating one of the four compounds into the 3'-end of the growing nucleic acid chain;

(5) removing the solution phase of the reaction system in the previous step, keeping the duplex linked to the support, and adding two different luciferases to carry out the ligation reaction, wherein the two luciferases can be specifically ligated with the first molecular label and the second molecular label, respectively;

(6) removing unbound luciferase by using an elution buffer;

(7) adding a substrate of the first luciferase and detecting fluorescence signal at the same time;

(8) removing the solution of the previous step reaction;

(9) adding a substrate of the second luciferase and detecting fluorescence signal at the same time;

(10) removing the solution of the previous step reaction;

(11) removing the molecular label and 3'-protecting group of each nucleotide;

(12) optionally removing the solution of the previous step reaction;

(13) optionally repeating steps (3) to (12) to obtain sequence information of the nucleic acid molecule.

In a specific embodiment, the ligation of the two luciferases with nucleotides can also be carried out separately. For example, the first luciferase that is firstly labeled can be added first to allow it to undergo a ligation reaction with the nucleotide labeled with the first molecule, then the unbound first luciferase is removed by using use the elution buffer, the substrate of the first luciferase is added, and the fluorescent signal is detected at the same time; then, the second luciferase that is secondly labeled can be added to allow it to undergo a ligation reaction with the nucleotide labeled with the second molecule, then the unbound second luciferase is removed by using the elution buffer, the substrate of the second luciferase is added, and the fluorescent signal is detected at the same time. Specifically, the present invention provides a method for sequencing a nucleic acid molecule, which comprises the following steps:

(1) providing a nucleic acid molecule to be sequenced that is linked to a support, or linking a nucleic acid molecule to be sequenced to a support;

(2) adding a primer for initiating a nucleotide polymerization reaction, a polymerase for performing the nucleotide polymerization reaction, and four compounds to form a reaction system containing a solution phase and a solid phase; wherein, the four compounds are respectively derivatives of nucleotides A, (T/U), C and G, and have the ability of base complementary pairing; and, the hydroxyl (—OH) at the 3'-position of ribose or deoxyribose of the four compounds is protected by a protecting group; and, the first compound is linked with a first molecular label, the second compound is linked with a second molecular label, the third compound is linked with a first molecular label and a second molecular label, or a part of the third compound is linked with a first molecular label and another part of the third compound is linked with a second molecular label, the fourth compound is not linked with any molecular label;

(3) annealing the primer to the nucleic acid molecule to be sequenced, and forming a duplex linked to the support by using the primer as an initial growing nucleic acid chain together with the nucleic acid molecule to be sequenced;

(4) using the polymerase to carry out the nucleotide polymerization reaction under a condition that allows the polymerase to carry out the nucleotide polymerization reaction, thereby incorporating one of the four compounds into the 3'-end of the growing nucleic acid chain;

(5) removing the solution phase of the reaction system in the previous step, keeping the duplex linked to the support, and adding a first luciferase to perform a ligation reaction, wherein the first luciferase can specifically bind to the first molecular label;

(6) removing unbound first luciferase by using an elution buffer;

(7) adding a substrate of the first luciferase and detecting fluorescence signal at the same time;

(8) removing the solution of the previous step reaction;

(9) adding a second luciferase to perform a ligation reaction, wherein the second luciferase can specifically bind to the second molecular label;

(10) removing unbound second luciferase by using an elution buffer;

(11) adding a substrate of the second luciferase and detecting fluorescence signal at the same time;

(12) removing the solution of the previous step reaction;

(13) optionally removing the molecular label and 3'-protecting group of each nucleotide;

(14) optionally repeating steps (3) to (13) or (3) to (11) one or more times to obtain sequence information of the nucleic acid molecule.

In a specific embodiment, the two luciferases can be the same, which can specifically bind to the first molecular label and the second molecular label respectively, that is, only one luciferase and substrate are used, and the first luciferase that is firstly labeled and the second luciferase that is secondly labeled are separately ligated to the nucleotide. For example, the first luciferase that is firstly labeled is firstly added, it is allowed to undergo the ligation reaction with the nucleotide labeled with the first molecule, then the unbound first luciferase is removed with the elution buffer, the substrate of the luciferase is added, and the fluorescent signal is detected at the same time; then the second luciferase that is secondly labeled is added, it is allowed to undergo the ligation reaction with the nucleotide labeled with the second molecule, then the unbound second luciferase was removed with the elution buffer, the substrate of the luciferase is added, and the fluorescence signal is at the same time. Specifically, the present invention provides a method for sequencing a nucleic acid molecule, which comprises the following steps:

(1) providing a nucleic acid molecule to be sequenced that is linked to a support, or linking a nucleic acid molecule to be sequenced to a support;

(2) adding a primer for initiating a nucleotide polymerization reaction, a polymerase for performing the nucleotide polymerization reaction, and four compounds to form a reaction system containing a solution phase and a solid phase; wherein, the four compounds are respectively derivatives of nucleotides A, (T/U), C and G, and have the ability of base complementary pairing; and, the hydroxyl (—OH) at the 3'-position of ribose or deoxyribose of the four compounds is protected by a protecting group; and, the first compound is linked with a first molecular label, the second compound is linked with a second molecular label, the third compound is linked with a first molecular label and a second molecular label, or a part of the third compound is linked with a first molecular label and another part of the third compound is linked with a second molecular label, the fourth compound is not linked with any molecular label;

(3) annealing the primer to the nucleic acid molecule to be sequenced, and forming a duplex linked to the support by using the primer as an initial growing nucleic acid chain together with the nucleic acid molecule to be sequenced;

(4) using the polymerase to carry out the nucleotide polymerization reaction under a condition that allows the polymerase to carry out the nucleotide polymerization reaction, thereby incorporating one of the four compounds into the 3'-end of the growing nucleic acid chain;

(5) removing the solution phase of the reaction system in the previous step, keeping the duplex linked to the support, and adding a first luciferase to perform a ligation reaction, wherein the first luciferase can specifically bind to the first molecular label;
(6) removing unbound first luciferase by using an elution buffer;
(7) adding a substrate of the luciferase and detecting fluorescence signal at the same time;
(8) removing the solution of the previous step reaction;
(9) adding a reagent for denaturing the luciferase;
(10) removing the solution of the previous step reaction;
(11) adding a second luciferase to perform a ligation reaction, wherein the second luciferase can specifically bind to the second molecular label;
(12) removing unbound second luciferase by using an elution buffer;
(13) adding a substrate of the luciferase and detecting fluorescence signal at the same time;
(14) optionally removing the solution of the previous step reaction;
(15) optionally removing the molecular label and 3'-protecting group of each nucleotide;
(16) optionally repeating steps (3) to (15) or (3) to (13) one or more times to obtain sequence information of the nucleic acid molecule.

In another aspect, the present invention also relates to a kit for sequencing a polynucleotide, which comprises:

(a) four compounds, the four compounds are respectively derivatives of nucleotides A, (T/U), C and G, and have the ability of base complementary pairing; and, the hydroxyl (—OH) at the 3'-position of ribose or deoxyribose of the four compounds is protected by a protecting group; and,
the first compound is linked with a first molecular label,
the second compound is linked with a second molecular label,
the third compound is linked with a first molecular label and a second molecular label, or part of the third compound is linked with a first molecular label and another part of the third compound is linked with a second molecular label,
the fourth compound is not linked with any molecular label; and
(b) two luciferases, the two luciferases can specifically bind to the first molecular label and the second molecular label, respectively, and the two luciferases can be the same or different.

In some preferred embodiments, the kit of the present invention further comprises: a reagent and/or device for extracting a nucleic acid molecule from a sample; a reagent for pretreating the nucleic acid molecule; a support for linking the nucleic acid molecule to be sequenced; a reagent for linking (for example, covalently or non-covalently linking) the nucleic acid molecule to be sequenced to the support; a primer for initiating a nucleotide polymerization reaction; a polymerase for performing the nucleotide polymerization reaction; one or more buffer solutions; one or more washing solutions; or any combination thereof.

DETAILED DESCRIPTION

Unless otherwise defined, all technical and scientific terms used herein have the same meanings as commonly understood by those skilled in the art to which the present invention pertains. All patents, applications and other publications mentioned herein are incorporated by reference in their entirety. If the definitions set forth herein conflict or are inconsistent with the definitions described in the patents, applications and other publications incorporated herein by reference, the definitions described herein shall prevail.

As used herein, the term "polynucleotide" refers to deoxyribonucleic acid (DNA), ribonucleic acid (RNA), or analogs thereof. Polynucleotides can be single-stranded, double-stranded, or comprise both single-stranded and double-stranded sequences. Polynucleotide molecules can be derived from double-stranded form of DNA (dsDNA) (for example, genomic DNA, PCR and amplification products, etc.), or can be derived from single-stranded form of DNA (ssDNA) or RNA and can be converted into dsDNA form, and vice versa. The exact sequence of the polynucleotide molecule can be known or unknown. The following are illustrative examples of polynucleotides: gene or gene fragment (for example, probe, primer, EST or SAGE tag), genomic DNA, genomic DNA fragment, exon, intron, messenger RNA (mRNA), transport RNA, ribosomal RNA, ribozyme, cDNA, recombinant polynucleotide, synthetic polynucleotide, branched polynucleotide, plasmid, vector, isolated DNA of any sequence, isolated RNA of any sequence, and nucleic acid probe, primer or amplified copy of any of the above sequences.

Polynucleotides may include nucleotides or nucleotide analogs. Nucleotide usually comprises a saccharide (i.e., ribose or deoxyribose), a base, and at least one phosphate group. Nucleotide can be abasic (i.e. free of base). Nucleotide includes deoxyribonucleotide, modified deoxyribonucleotide, ribonucleotide, modified ribonucleotide, peptide nucleotide, modified peptide nucleotide, modified phosphate saccharide backbone nucleoside and mixtures thereof. Examples of nucleotide include, for example, adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine triphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP) and deoxyuridine triphosphate (dUTP). Nucleotide analogs containing modified bases can also be used in the methods described herein. Whether it has a natural backbone or a similar structure, exemplary modified base that can be comprised in the polynucleotide includes, for example, inosine, xathanine, hypoxathanine, isocytosine, isoguanine, 2-aminopurine, 5-methylcytosine, 5-hydroxymethylcytosine, 2-aminoadenine, 6-methyladenine, 6-methylguanine, 2-propylguanine, 2-propyladenine, 2-thiouracil, 2-thiothymine, 2-thiocytosine, 15-halogenated uracil, 15-halogenated cytosine, 5-propynyluracil, 5-propynylcytosine, 6-azouracil, 6-azocytosine, 6-azothymine, 5-uracil, 4-thiouracil, 8-halogenated adenine or guanine, 8-aminoadenine or 8-aminoguanine, 8-thioadenine or 8-thioguanine, 8-thioalkyladenine or 8-thioalkylguanine, 8-hydroxyadenine or 8-hydroxyguanine, 5-halogenated uracil or cytosine, 7-methylguanine, 7-methyladenine, 8-azaguanine, 8-azaadenine, 7-deazaguanine, 7-deazaadenine, 3-deazaguanine, 3-deazaadenine, etc. As known in the art, certain nucleotide analogs, for example, nucleotide analogs such as adenosine 5'-phosphoryl sulfate, cannot be incorporated into polynucleotide.

Generally speaking, nucleotides include nucleotides A, C, G, T or U. As used herein, the term "nucleotide A" refers to a nucleotide containing adenine (A) or a modifier or analog thereof, such as ATP, dATP. "Nucleotide G" refers to a nucleotide containing guanine (G) or a modifier or analog thereof, such as GTP, dGTP. "Nucleotide C" refers to a nucleotide containing cytosine (C) or a modifier or analog thereof, such as CTP, dCTP. "Nucleotide T" refers to a nucleotide containing thymine (T) or a modifier or analog thereof, such as TTP, dTTP. "Nucleotide U" refers to a nucleotide containing uracil (U) or a modifier or analog thereof, such as UTP, dUTP.

Labeling of Nucleotide

The present invention relates to labeling nucleotide with different labels, individually or in combination, so that different luciferases can be ligated to the nucleotide. As used herein, the molecular label for labeling nucleotide and the label specifically binding thereto may be any pairing molecules that can specifically bind to each other. The specific binding between the pairing members realizes the ligation of nucleotide to luciferase. Exemplary pairing members include but are not limited to: (a) hapten or antigenic compound combined with the corresponding antibody or its binding part or fragment, such as digoxin-digoxin antibody, N3G-N3G antibody, FITC-FITC antibody; (b) nucleic acid aptamer and protein; (c) non-immune binding pair (for example, biotin-avidin, biotin-streptavidin, biotin-neutravidin); (d) hormone-hormone binding protein; (e) receptor-receptor agonist or antagonist; (f) lectin-carbohydrate; (g) enzyme-enzyme cofactor; (h) enzyme-enzyme inhibitor; and (i) a pair of complementary oligonucleotides or polynucleotides capable of forming a nucleic acid duplex.

In a specific embodiment, the first molecular label and the second molecular label are small molecular labels, which are selected from biotin, digoxin, N3G or FITC. The two luciferases can specifically bind to the first molecular label and the second molecular label, respectively. For example, in a specific embodiment, the first molecular label is biotin, then the first luciferase can be streptavidin-labeled luciferase; the second molecular label is digoxin, the second luciferase can be a digoxin antibody-labeled luciferase that is different from the first luciferase, and the second luciferase may also be a digoxin antibody-labeled luciferase that is the same as the first luciferase. The source of the luciferase includes, but is not limited to, firefly, gaussia, Renilla and other organisms. For example, the streptavidin-labeled luciferase may be SA-Gluc: Streptavidin-Gaussia princeps luciferase from Adivity Company. The digoxin antibody-labeled luciferase may be digoxin antibody-Gluc or digoxin antibody-Nluc.

As used herein, the expression "first compound is linked with a first molecular label" means that all of the first compound are linked with the first molecular label, or part of the first compound are linked with the first molecular label while the rest of the first compound are not linked with the molecular label. In the same way, the expression "second compound is linked with a second molecular label" means that all of the second compound are linked with the second molecular label, or part of the second compound are linked with the second molecular label while the rest of the second compound are not linked with the molecular label. The expression "third compound is linked with a first molecular label and a second molecular label" means that all of the third compound are linked with the first molecular label and the second molecular label, or part of the third compound are linked with the first molecular label and the second molecular label while the rest of the third compound are not linked with the molecular labels.

Sequencing of Polynucleotide

Preferably, the nucleotides ligated with different luciferases of the present invention are suitable for sequencing by synthesis. Sequencing by synthesis methods as used herein are various sequencing by synthesis methods well known in the art. Basically, sequencing by synthesis involves: first hybridizing a nucleic acid molecule to be sequenced with a sequencing primer, and then in the presence of a polymerase, polymerizing a nucleotide ligated with different luciferase as described herein at the 3'-end of the sequencing primer by using the nucleic acid molecule to be sequenced as a template. After polymerization, the nucleotide is identified by detecting the fluorescent signal emitted by the luciferase. After the luciferase is removed from the labeled nucleotide, the next polymer sequencing cycle is performed.

The method for determining the sequence of a target polynucleotide can be carried out as follows: denaturing the target polynucleotide sequence, contacting the target polynucleotide with different nucleotides, respectively, so as to form a complement of the target nucleotide, and detecting the incorporated nucleotide. The method utilizes polymerization, which allows the polymerase to extend the complementary strand by incorporating the correct nucleotides complementary to the target. The polymerization reaction also requires a special primer to initiate polymerization.

For each round of reaction, the incorporation of the nucleotide is carried out by polymerase, and the incorporation event is then measured. There are many different polymerases, and it is easy for a person of ordinary skill in the art to determine the most suitable polymerase. Preferred enzymes include DNA polymerase I, Klenow fragment, DNA polymerase III, T4 or T7 DNA polymerase, Taq polymerase or vent polymerase. It is also possible to use polymerases engineered to have specific properties.

The sequencing method is preferably performed on the target polynucleotide arranged on a solid support. Through linker molecules, a plurality of target polynucleotides can be immobilized on the solid support, or can be attached to particles such as microspheres, and the particles can also be attached to a solid support material.

The polynucleotide can be attached to a solid support by a variety of methods, including the use of biotin-streptavidin interaction. Methods for immobilizing polynucleotides on a solid support are well known in the art, and include lithography techniques and spotting each polynucleotide at a specific position on the solid support. Suitable solid supports are known in the art and include glass slides and beads, ceramic and silicon surfaces, and plastic materials. The support is usually flat, although microbeads (microspheres) can also be used, and the latter can also be attached to other solid supports by known methods. The microspheres can have any suitable size, and their diameter is usually 10 to 100 nanometers. In a preferred embodiment, the polynucleotide is directly attached on a flat surface, preferably on a flat glass surface. The linking is preferably carried out in the form of a covalent bond. The array used is preferably a single molecule array, which includes polynucleotides located in unique optically resolvable regions, for example, as described in the International Application No. WO00/06770.

The necessary conditions for polymerization are well known to those skilled in the art. In order to perform the polymerase reaction, usually a primer sequence should be firstly annealed to the target polynucleotide. The primer sequence is recognized by the polymerase and serves as the initiating site for the subsequent extension of the complementary strand. The primer sequence may be added as an independent component relative to the target polynucleotide. In addition, the primer and the target polynucleotide may each be a part of a single-stranded molecule, and the primer part and a part of the target form an intramolecular duplex, that is, a hairpin loop structure. The structure can be immobilized on the solid support through any position of the molecule. Other conditions necessary for the polymerase reaction are well known to those skilled in the art, and these conditions include temperature, pH, and buffer composition.

Subsequently, the labeled nucleotides of the present invention are brought into contact with the target polynucleotide to enable polymerization. The nucleotides can be added sequentially, that is, each type of nucleotide (A, C, G or T/U) is added separately, or added at the same time.

The polymerization step is allowed to proceed for a time sufficient to incorporate one nucleotide.

Then, the unincorporated nucleotides are removed, for example, by removing the solution phase of the reaction system in the previous step, leaving the duplexes attached to the support.

Subsequently, two luciferases containing different luciferases can be added to carry out a ligation reaction. The two luciferases can specifically bind to the molecular labels for labeling nucleotides respectively, thereby realizing the ligation of the luciferase to the incorporated nucleotide. Then by adding the corresponding substrates of the luciferases and detecting the fluorescent signal, the identification of the incorporated nucleotide is achieved. It is also possible to add two kinds of luciferases containing the same luciferase to carry out the ligation reaction. The luciferases can specifically bind to the molecular labels for labeling nucleotides respectively, thereby realizing the ligation of the luciferase to the incorporated nucleotide. Then by adding the corresponding substrate of the luciferase and detecting the fluorescent signal, the identification of the incorporated nucleotide is realized.

In a specific embodiment, four deoxyribonucleotide analogs are labeled with different small molecule labels, i.e., biotin (abbreviated as B) and digoxin (abbreviated as D), for example, nucleotide A is labeled with B, nucleotide C is labeled with B and D, nucleotide T is labeled with D, and nucleotide G is not labeled. The 3'-end hydroxyl groups of the four deoxyribonucleotide analogs labeled with different small molecules are all blocked to ensure that only one deoxyribonucleotide is bound during each sequencing reaction. During the sequencing reaction, a mixture of the four labeled deoxyribonucleotide analogues and the sequencing polymerase is first introduced, under the action of the polymerase, one deoxyribonucleotide analogue is incorporated into the 3'-end of the growing nucleic acid chain according to the principle of base complementary pairing. By removing the solution phase of the reaction system in the previous step, leaving the duplex linked to the support, the unbound deoxyribonucleotide analogs can be removed. Then, two luciferases containing different luciferases are added, wherein the first luciferase is labeled with streptavidin, which binds to nucleotide A or nucleotide C labeled with small molecule B, and the second luciferase is labeled with digoxin antibody, which binds to the nucleotide C or the nucleotide T labeled with a small molecule D. After removing the unbound luciferases with an elution buffer, a substrate of the first luciferase is added, the nucleotide ligated with the first luciferase emits light, and the signal is detected by a detector; a substrate of the second luciferase is added, the nucleotide ligated with the second luciferase emits light, and the signal is detected by a detector, so that the luminescence shown in the following table is obtained, and the base can be identified.

| | First detection | Second detection |
|---|---|---|
| A | 1 | 0 |
| C | 1 | 1 |
| G | 0 | 0 |
| T | 0 | 1 |

In a specific embodiment, the ligation of two luciferases containing different luciferases to the labeled nucleotides and signal detection can be performed separately. First, the first luciferase is added, which is labeled with streptavidin, and binds to nucleotide A or nucleotide C labeled with small molecule B. After removing the unbound first luciferase with the elution buffer, the substrate of the first luciferase is added, the nucleotide ligated with the first luciferase emits light, and the signal is detected by a detector. After removing the reaction solution, a second luciferase labeled with digoxin antibody is added, which binds to nucleotide C or nucleotide T labeled with small molecule D, and then the unbound second luciferase is removed with elution buffer, a substrate of the second luciferase is added, the nucleotide ligated with the second luciferase emits light, and the signal is detected by a detector. Thus, the luminescence shown in the table above is obtained, and the identification of bases can be performed.

In another specific embodiment, the ligation of the two luciferases containing the same luciferase to the labeled nucleotides and the signal detection are performed separately. First, the first luciferase is added, which is labeled with streptavidin, and binds to nucleotide A or nucleotide C labeled with small molecule B. After removing the unbound first luciferase with an elution buffer, a substrate of the luciferase is added, the nucleotide ligated with the first luciferase emits light, and the signal is detected by a detector. Then, a reagent that denatures the first luciferase is added; after removing the reaction solution, the second luciferase is added, which is labeled with digoxin antibody, and binds to nucleotide C or nucleotide T labeled with small molecule D, then the unbound second luciferase is removed by using an elution buffer, a substrate of the luciferase is added, the base ligated with the second luciferase emits light, and the signal is detected by a detector. Thus, the luminescence shown in the table above is obtained, and the identification of bases can be performed.

Detection of Fluorescence Signal

The way of detecting fluorescent signal is well known in the art. For example, it can be realized by a device that detects the wavelength of fluorescence. Such devices are well known in the art. For example, such a device may be a confocal scanning microscope that scans the surface of a solid support with a laser in order to image the fluorophore directly bound to the nucleic acid molecule to be sequenced. In addition, a sensitive 2-D detector, such as a charge-coupled detector (CCD), can be used to observe each signal generated, for example. Other techniques such as Scanning Near Field Optical Microscopy (SNOM) can also be used, for example.

Removing of Label

After the detection, suitable conditions can be used to remove the label attached to the nucleotides.

In a specific embodiment, the labeled nucleotides of the present invention also have a 3'-protecting group. In some embodiments of the present invention, the protecting group and the label are usually two different groups on the 3'-blocked labeled nucleotide, but in other embodiments, the protecting group and the label may also be the same group.

As used herein, the term "protecting group" refers to a group that prevents a polymerase (which incorporates a nucleotide containing the group into a polynucleotide chain being synthesized) from unceasingly catalyzing the incorporation of another of nucleotide after the nucleotide containing the group has being incorporated into the polynucleotide chain being synthesized. Such protecting group is also referred to herein as 3'-OH protecting group. The nucleotide containing such protecting group is also referred to herein as 3'-blocked nucleotide. The protecting group can be any suitable group that can be added to nucleotide, as long as the protecting group can prevent additional nucleotide molecule from being incorporated into the polynucleotide chain and can be easily removed from saccharide portion of the nucleotide without damaging the polynucleotide chain. In addition, the nucleotide modified with the protecting group needs to be resistant to polymerases or other suitable enzymes for incorporating the modified nucleotide into the polynucleotide chain. Therefore, the ideal protecting group exhibits long-term stability, can be efficiently incorporated by polymerase, prevents secondary or further incorporation of nucleotides, and can removed under mild conditions, preferably under aqueous conditions, that do not damage the structure of the polynucleotide.

The prior art has described a variety of protecting groups that meet the above description. For example, WO 91/06678 discloses that 3'-OH protecting groups include esters and ethers, —F, $—NH_2$, $—OCH_3$, $—N_3$, $—OPO_3$, $—NHCOCH_3$, 2-nitrophenyl carbonate, 2,4-hyposulfonyl-dinitro and tetrahydrofuran ether. Metzker et al. (Nucleic Acids Research, 22(20): 4259-4267, 1994) discloses the synthesis and application of eight 3'-modified 2-deoxyribonucleoside 5'-triphosphates (3'-modified dNTPs). WO2002/029003 describes the use of allyl protecting group to cap 3'-OH group of growing DNA strand in a polymerase reaction. Preferably, various protecting groups reported in the International Application Publications WO2014139596 and WO2004/018497 can be used, including, for example, those protecting groups illustrated in FIG. 1A and those 3'-hydroxyl protecting groups (i.e., protecting groups) defined in the claims of WO2014139596, and for example, those protecting groups illustrated in FIGS. 3 and 4 and those defined in the claims of WO2004/018497. The above references are all incorporated herein by reference in their entirety.

Those skilled in the art will understand how to attach a suitable protecting group to ribose ring in order to block the interaction with 3'-OH. The protecting group can be directly attached to the 3'-position, or can be attached to the 2'-position (the protecting group has sufficient size or charge to block the interaction at the 3'-position). In addition, the protecting group can be attached at the 3'- and 2'-positions, and can be cleaved to expose the 3'-OH group.

After successfully incorporating the 3'-blocked nucleotide into the growing nucleic acid chain, the sequencing protocol requires the removal of the protecting group to generate a usable 3'-OH site for continuous chain synthesis. The reagents that can remove protecting groups from modified nucleotides as used herein depend to a large extent on the protecting groups used. For example, removing an ester protecting group from the 3'-hydroxyl group is usually achieved by alkaline hydrolysis. The ease of removal of protecting groups varies greatly; generally, the greater the electronegativity of the substituent on the carbonyl carbon, the greater the ease of removal. For example, highly electronegative trifluoroacetic acid group can be rapidly cleaved from the 3'-hydroxyl group at pH 7 in methanol (Cramer et al., 1963), so it is unstable during polymerization at this pH. Phenoxyacetate group is cleaved within less than 1 minute, but a significantly higher pH is required, for example, by using NH-/methanol (Reese and Steward, 1968). Various hydroxy protecting groups can be selectively cleaved using chemical methods other than alkaline hydrolysis. 2,4-Dinitrophenylthio group can be quickly cleaved by treatment with nucleophiles such as thiophenol and thiosulfate (Letsinger et al., 1964). Allyl ether can be cleaved by treatment with Hg(II) in acetone/water (Gigg and Warren, 1968). Tetrahydrothianyl ether can be removed under neutral conditions with Ag(I) or Hg (II) (Cohen and Steele, 1966; Cruse et al., 1978). Photochemical deblocking can be used with photochemically cleavable protecting groups. There are several protecting groups that can be used in this method. The use of o-nitrobenzyl ether as a protecting group for the 2'-hydroxyl functionality of ribonucleoside is known and confirmed (Ohtsuka et al., 1978); and it is removed by irradiation at 260 nm. The protecting group of alkyl carbonate o-nitrobenzyl carbonate is also removed by irradiation at pH 7 (Cama and Christensen, 1978). Enzymatic deblocking of the 3'-OH protecting group is also possible. It has been demonstrated that T4 polynucleotide kinase can convert the 3'-phosphate end into 3'-hydroxyl end, which can then be used as a primer for DNA polymerase I (Henner et al., 1983). This 3'-phosphatase activity is used to remove the 3'-protecting group of those dNTP analogs containing phosphate as the protecting group.

Other reagents that can remove protecting groups from 3'-blocked nucleotides include, for example, phosphines (for example, tris(hydroxymethyl)phosphine (THP)), which can, for example, remove 3'-OH protecting group containing azide from nucleotide (for this application of phosphine, see, for example, the description in WO2014139596, the entire content of which is incorporated herein by reference). Other reagents that can remove protecting groups from 3'-blocked nucleotides also include, for example, the corresponding reagents described on pages 114-116 in the description of WO2004/018497 for removing 3'-allyl, 3,4-dimethoxybenzyloxymethyl or fluoromethoxymethyl that is used as 3'-OH protecting group.

In an embodiment of the present invention, the label of nucleotide is preferably removed together with the protecting group after detection.

In certain embodiments, the label may be incorporated into a protecting group, thereby allowing it is removed along with the protecting group after the 3'-blocked nucleotide is incorporated into the nucleic acid chain.

In other embodiments, the label can be attached to the nucleotide using a linking group and a protecting group separately. Such a label may, for example, be attached to the purine or pyrimidine base of the nucleotide. In certain embodiments, the linking group used is cleavable. The use of a cleavable linking group ensures that the label can be removed after detection, which avoids any signal interference with any labeled nucleotides subsequently incorporated. In other embodiments, a non-cleavable linking group can be used, because after the labeled nucleotide is incorporated into the nucleic acid chain, subsequent nucleotide incorporation is not needed, so there is no need to remove the label from the nucleotide.

In other embodiments, the label and/or linking group may have a size or structure sufficient to block the incorporation of other nucleotides into the polynucleotide chain (that is, the label itself can serve as a protecting group). The blocking may be due to steric hindrance, or it may be due to a combination of size, charge and structure.

The cleavable linking groups are well known in the art, and conventional chemical methods can be used to link the linking group to the nucleotide base and the label. The linking group can be attached to any position of the nucleotide base, provided that Watson-Crick base pairing can still be performed. For purine bases, it is preferred that the linking group is attached through position 7 of the purines or the preferred deaza-purine analogs, through 8-modified purines, through N-6 modified adenines or N-2 modified guanines. For pyrimidines, it is preferred to link through position 5 of cytosine, thymine and uracil, and position N-4 of cytidine.

The use of the term "cleavable linking group" does not mean that the entire linking group needs to be removed (for example, from the nucleotide base). When the label is attached to the base, the nucleoside cleavage site can be located at a position on the linking group, which position can ensure that a part of the linking group remains attached to the nucleotide base after cleavage.

Suitable linking groups include, but are not limited to, disulfide linking groups, acid-labile linking groups (including dialkoxybenzyl linking groups, Sieber linking groups, indole linking groups, tert-butyl Sieber linking groups), electrophilic cleavable linking groups, nucleophilic cleavable linking groups, photo-cleavable linking groups, linking groups that can be cleaved under reducing and oxidizing conditions, safety-catch linking groups, and linking groups that can be cleaved through elimination mechanisms. Suitable linking groups can be modified with standard chemical protecting groups, as disclosed in the following documents: Greene & Wuts, protecting groups in Organic Synthesis, John Wiley & Sons. Guillier et al. disclosed other suitable cleavable linking groups for solid phase synthesis (Chem. Rev. 100:2092-2157, 2000).

The linking group can be cleaved by any suitable method, including exposure to acids, bases, nucleophiles, electrophiles, free radicals, metals, reducing or oxidizing reagents, light, temperature, enzymes, etc., and suitable methods for cleaving various cleavable linking groups will be exemplarily described below. Generally, the cleavable linking group can be cleaved under the same conditions as that of the protecting group, so that only one treatment is required to remove the label and the protecting group.

The linking group for electrophilic cleavage is typically cleaved by proton, which includes acid-sensitive cleavage. Suitable electrophilic cleavable linking groups include modified benzyl systems such as trityl, p-hydrocarbonyloxybenzyl ester, and p-hydrocarbonyloxybenzyl amide. Other suitable linking groups include tert-butoxycarbonyl (Boc) groups and acetal systems. To prepare suitable linking molecules, it is also possible to consider the use of thiophilic metals such as nickel, silver or mercury in the cleavage of thioacetals or other sulfur-containing protecting groups. The linking group for nucleophilic cleavage includes a group that is unstable in water (i.e., can be simply cleaved at alkaline pH), such as ester, and a group that is unstable to non-aqueous nucleophile. Fluoride ions can be used to cleave silicon-oxygen bonds in groups such as triisopropylsilane (TIPS) or tert-butyldimethylsilane (TBDMS). Photolyzable linking groups are widely used in saccharide chemistry. Preferably, the light required to activate cleavage does not affect other components in the modified nucleotide. For example, if a fluorophore is used as a label, it is preferable that the fluorophore absorbs light of a different wavelength than the light required to cleave the linking molecule. Suitable linking groups include those based on O-nitrobenzyl compounds and nitroveratryl compounds. Linking groups based on benzoin chemistry can also be used (Lee et al., J. Org. Chem. 64:3454-3460, 1999). A variety of linking groups that are sensitive to reductive cleavage are known. Catalytic hydrogenation using palladium-based catalysts has been used to cleave benzyl and benzyloxycarbonyl groups. Disulfide bond reduction is also known in the art. Methods based on oxidation are well known in the art. These methods include the oxidation of hydrocarbonyloxybenzyl group and the oxidation of the linking groups based on sulfur and selenium. It is also within the scope of the present invention to use aqueous iodine to cleave disulfide and other sulfur- or selenium-based linking groups. Safety-catch linkers are those that are cleaved in two steps. In a preferred system, the first step is the generation of a reactive nucleophilic center, and the subsequent second step involves intramolecular cyclization, which results in cleavage. For example, the levulinate linkage can be treated with hydrazine or photochemical methods to release an active amine, and the amine is then cyclized to cleave the ester elsewhere in the molecule (Burgess et al., J. Org. Chem. 62: 5165-5168, 1997). Elimination reactions can also be used to cleave the linking groups. Base-catalyzed elimination of groups such as fluorenylmethoxycarbonyl and cyanoethyl and palladium-catalyzed reductive elimination of allyl systems can be used.

In certain embodiments, the linking group may comprise a spacer unit. The length of the linking group is not important, as long as the label and the nucleotide are kept at a sufficient distance so as not to interfere with the interaction between the nucleotide and the enzyme.

In certain embodiments, the linking group may consist of a functional group similar to the 3'-OH protecting group. This will allow only single treatment is required to remove the label and the protecting group. A particularly preferred linking group is an azide-containing linking group that can be cleaved by phosphine.

The reagents that can remove the label from the modified nucleotide as used herein depend to a large extent on the label used. For example, in the case where a protecting group is incorporated into the label, a reagent for removing the protecting group described above is used to remove the label. Alternatively, when the label is attached to the base of the nucleotide through a cleavable linking group, the label is removed using a reagent that cleaves the linking group as described above. In a preferred embodiment, the same reagent is used to remove the label and the protecting group from the modified nucleotide, for example, in the case that the linking group consists of a functional group similar to the 3'-OH protecting group.

Kit

The present invention also provides a kit for sequencing a polynucleotide, which comprises:

(a) four compounds, the four compounds are respectively derivatives of nucleotides A, (T/U), C and G, and have the ability of base complementary pairing; and, the hydroxyl group (—OH) at the 3'-position of ribose or deoxyribose of the four compounds is protected by a protecting group; and, the first compound is linked with a first molecular label, the second compound is linked with a second molecular label, the third compound is linked with a first molecular label and a second molecular label, or part of the third compound is linked with a first molecular label and another part of the third compound is linked with a second molecular label, the fourth compound is not linked with any molecular label; and (b) two different luciferases, the two luciferases can specifically bind the first molecular label and the second molecular label respectively.

In a specific embodiment, the molecular labels used to label the four compounds and the labels used to label the two luciferases are as defined above.

In some preferred embodiments, the kit of the present invention further comprises: a reagent and/or device for extracting a nucleic acid molecule from a sample; a reagent for pretreating the nucleic acid molecule to be sequenced; a support for linking the nucleic acid molecule to be sequenced; a reagent for linking (for example, covalently or non-covalently linking) the nucleic acid molecule to be sequenced to the support; a primer for initiating a nucleotide polymerization reaction; a polymerase for carrying out the nucleotide polymerization reaction; one or more buffer solutions; one or more washing solutions; or any combination thereof.

In some preferred embodiments, the kit of the present invention further comprises a reagent and/or device for extracting a nucleic acid molecule from a sample. Methods for extracting nucleic acid molecules from samples are well known in the art. Therefore, various reagents and/or devices for extracting nucleic acid molecules, such as reagents for disrupting cells, reagents for precipitating DNA, reagents for washing DNA, reagents for dissolving DNA, reagents for precipitating RNA, reagents for washing RNA, reagents for dissolving RNA, reagents for removing proteins, reagents for removing DNA (for example, when the target nucleic acid molecule is RNA), reagents for removing RNA (for example, when the target nucleic acid molecule is DNA), and any combination thereof, can be configured in the kit of the present invention as required.

In some preferred embodiments, the kit of the present invention further comprises a reagent for pretreating nucleic acid molecule. In the kit of the present invention, the reagents used for pretreating nucleic acid molecules are not subject to additional restrictions, and can be selected according to actual needs. The reagents used for pretreatment of nucleic acid molecules include, for example, reagents for fragmentating nucleic acid molecules (for example, DNase I), reagents for complementing the ends of nucleic acid molecules (for example, DNA polymerase, such as T4 DNA polymerase, Pfu DNA polymerase, Klenow DNA polymerase), linker molecules, tag molecules, reagents for linking linker molecules with target nucleic acid molecules (for example, ligase, such as T4 DNA ligase), reagents for repairing nucleic acid nicks (for example, DNA polymerase that loses 3'-5' exonuclease activity but shows 5'-3' exonuclease activity), reagents for amplifying nucleic acid molecules (for example, DNA polymerase, primer, dNTP), reagents (for example, chromatography columns) for separating and purifying nucleic acid molecules, and any combination thereof.

In some preferred embodiments, the kit of the present invention further comprises a support for linking a nucleic acid molecule to be sequenced. The support may have any technical features and any combination thereof described above in detail for the support.

For example, in the present invention, the support can be made of various suitable materials. Such materials include, for example, inorganic materials, natural polymers, synthetic polymers, and any combination thereof. Specific examples include, but are not limited to: cellulose, cellulose derivatives (for example, nitrocellulose), acrylic resin, glass, silica gel, polystyrene, gelatin, polyvinylpyrrolidone, copolymer of vinyl and acrylamide, and polystyrene cross-linked with, for example, divinylbenzene (see, for example, Merrifield Biochemistry 1964, 3, 1385-1390), polyacrylamide, latex, dextran, rubber, silicon, plastic, natural sponge, metal plastic, cross-linked dextran (for example, Sephadex™), agarose gel (Sepharose™), and other supports known to those skilled in the art.

In some preferred embodiments, the support used to link the nucleic acid molecule to be sequenced may be a solid support, including an inert substrate or matrix (for example, a glass slide, polymer beads, etc.). The inert substrate or matrix has been functionalized, for example, by applying intermediate materials containing reactive groups that allow the covalent attachment of biomolecules such as polynucleotides. Examples of such support include, but are not limited to, polyacrylamide hydrogels supported on an inert substrate such as glass, particularly the polyacrylamide hydrogels described in WO2005/065814 and US2008/0280773, wherein the contents of the patent applications are incorporated herein in its entirety by reference. In such embodiments, biomolecules (for example, polynucleotides) can be directly covalently attached to an intermediate material (for example, hydrogel), and the intermediate material itself can be non-covalently attached to the substrate or matrix (for example, glass substrate). In some preferred embodiments, the support is a glass slide or silicon wafer which surface is modified with a layer of avidin, amino, acrylamide silane or aldehyde-based chemical groups.

In the present invention, the support or solid support is not limited to its size, shape and configuration. In some embodiments, the support or solid support is of planar structure, such as slide, chip, microchip, and/or array. The surface of such support may be in the form of planar layer. In some embodiments, the support or its surface is non-planar, for example, the inner or outer surface of tube or container. In some embodiments, the support or solid support includes microspheres or beads. In certain preferred embodiments, the support used to link the nucleic acid molecules to be sequenced is an array of beads or wells.

In some preferred embodiments, the kit of the present invention further comprises a reagent for linking (for example, covalently or non-covalently linking) the nucleic acid molecule to be sequenced to the support. Such reagent includes, for example, reagents that activate or modify the nucleic acid molecule (for example, its 5'-end), such as phosphoric acid, thiol, amine, carboxylic acid or aldehyde; reagents that activate or modify the surface of the support, such as amino-alkoxysilane (for example, aminopropyltrimethoxysilane, aminopropyltriethoxysilane, 4-aminobutyltriethoxysilane, etc.); crosslinking agent, such as succinic anhydride, phenyl diisothiocyanate (Guo et al., 1994), maleic anhydride (Yang et al., 1998), 1-ethyl-3-(3-dimethylaminopropyl)-carbodiimide hydrochloride (EDC), meta-maleimidobenzoic acid-N-hydroxysuccinimide ester (MBS), N-succinimidyl[4-iodoacetyl]aminobenzoic acid (SIAB), succinimidyl 4-(N-maleimidomethyl)cyclohexane-1-carboxylate (SMCC), N-γ-maleimidobutyryloxy-succinimide ester (GMBS), succinimidyl 4-(p-maleimidophenyl) butyrate (SMPB); and any combination thereof.

In certain preferred embodiments, the kit of the present invention further comprises a primer for initiating the nucleotide polymerization reaction. In the present invention, the primer is not subjected to additional restrictions as long as it can specifically be annealed to a region of the target nucleic acid molecule. In some exemplary embodiments, the length of the primer may be 5-50 bp, such as 5-10, 10-15, 15-20, 20-25, 25-30, 30-35, 35-40, 40-45, 45-50 bp. In some exemplary embodiments, the primer may comprise naturally-occurring or non-naturally-occurring nucleotides. In some exemplary embodiments, the primer comprises or consists of naturally-occurring nucleotides. In some exemplary embodiments, the primer comprises a modified nucleotide, such as a locked nucleic acid (LNA). In certain preferred embodiments, the primer comprises a universal primer sequence.

In certain preferred embodiments, the kit of the present invention further comprises a polymerase for carrying out the nucleotide polymerization reaction. In the present invention, various suitable polymerases can be used. In some exemplary embodiments, the polymerase can use DNA as a template to synthesize a new DNA strand (for example, DNA polymerase). In some exemplary embodiments, the polymerase can use RNA as a template to synthesize a new DNA strand (for example, reverse transcriptase). In some exemplary embodiments, the polymerase can use DNA or RNA as a template to synthesize a new RNA strand (for example, RNA polymerase). Therefore, in certain preferred embodiments, the polymerase is selected from the group consisting of DNA polymerase, RNA polymerase, and reverse transcriptase.

In certain preferred embodiments, the kit of the present invention further comprises one or more buffer solutions. Such buffers include, but are not limited to, buffer solution for DNase I, buffer solution for DNA polymerase, buffer solution for ligase, buffer solution for eluting nucleic acid molecule, buffer solution for dissolving nucleic acid molecule, buffer solution for carrying out nucleotide polymerization reaction (for example, PCR), and buffer solution for ligation reaction. The kit of the present invention may comprise any one or more of the above-mentioned buffer solutions.

In certain preferred embodiments, the kit of the present invention further comprises one or more washing solutions. Examples of such washing solutions include, but are not limited to, phosphate buffer, citrate buffer, Tris-HCl buffer, acetate buffer, carbonate buffer, and the like. The kit of the present invention may comprise any one or more of the above-mentioned washing solutions.

Beneficial Effects of the Present Invention

Compared with the prior art, the technical solution of the present invention has the following beneficial effects:

(1) The method of the present invention uses only two molecular labels to realize the labeling of four nucleotides, and realizes self-luminescence by using luciferase. Therefore, the sequencing device used in the sequencing method of the present invention does not need to be equipped with an excitation light source, nor does it need to adopt an additional design to filter the background generated by the laser light source. On the one hand, the manufacturing cost of the sequencing device is greatly reduced, which is helpful for the promotion and application of the sequencing device and the sequencing method; on the other hand, the volume of the sequencing device is significantly reduced, making the sequencing device lighter and easier to carry.

(2) The 3'-hydroxyl group of the deoxyribonucleotide used in the sequencing method of the present invention is modified and blocked. During the sequencing process, only one deoxyribonucleotide can be synthesized per reaction, ensuring that only one deoxyribonucleotide can be incorporated per reaction, thereby improving the accuracy of sequencing.

Although the specific embodiments of the present invention have been described in detail, those skilled in the art will understand that various modifications and changes can be made to the details according to all the teachings that have been disclosed, and these changes are within the protection scope of the present invention. The full scope of the present invention is given by the appended claims and any equivalents thereof.

BRIEF DESCRIPTION OF THE DRAWINGS

FIG. 1: the procedure for the conjugation of antibody and Nluc, wherein the enzyme in the FIGURE referred to Nluc, and the antibody in the FIGURE referred to digoxin antibody.

EXAMPLES

Example 1

1. Construction of Sequencing Library (1) The following DNA sequence was designed:

(SEQ ID NO: 1)

GATATCTGCAGGCATAGAATGAATATTATTGAATCAATAATTA

AAGTCGGAGGCCAAGCGGTCTTAGGAAGACAACAACT

GCTTGGCTGCACAGAACGACATGGCTACGATCCGACTT

*TACAACTACG*ATAATGGGCTGGATACATGGAATGATTATAGA

TATATTAAGGAATAATGTTAATTAATGCCTAAATTAATTAATC

TAAGGGGGTTAATACTTCAGCCTGTGATATC.

For the convenience of library construction, oligo sequences (bold font) were added at the two ends of the sequence, and the linker sequence (shaded part) of BGISEQ-500 was inserted in the middle part, the italicized bold part showed the first 10 bp bases of the sequence to be sequenced. The above sequence was synthesized by GenScript Biotechnology Company, and for unlimited use of the sequence, the synthesized sequence was inserted into the pUC57 vector and transformed into *E. coli* cells.

(2) A suitable amount of *E. coli* containing a known library was cultured, and plasmids were extracted; the following pair of primers was designed: GATATCTGCAGGCAT (SEQ ID NO: 2, Primer 1), GATATCACAGGCTGA (SEQ ID NO: 3, Primer 2), the known sequence was amplified according to the following system (Table 1) and process (Table 2), and the PCR product was purified with magnetic beads. The purified PCR product was added with split oligo (ATGCCTGCAGATATCGATATCACAGGCTGA, SEQ ID NO: 4) and subjected to circularization and library construction according to instruction and process of the BGISEQ-500 SE50 circularization library construction kit (MGI) for later use;

TABLE 1

| (the enzymes were from BGI's own production) | | |
|---|---|---|
| | 1 | x |
| 5X high-fidelity enzyme reaction solution | 20 | µl |
| dNTPs mixure (each 10 mM) | 5 | µl |
| High-fidelity enzyme (1U/µl) | 1 | µl |
| Primer 1 (20 µM) | 6 | µl |
| Primer 2 (20 µM) | 6 | µl |
| Plasmid DNA template (20 ng/µl) | 1 | µl |
| Molecular water | 61 | µl |
| Total volume | 100 | µl |

TABLE 2

| | | |
|---|---|---|
| 98° C. | 3 min; | |
| 98° C. | 20 s | 33 cycles |
| 60° C. | 15 s | |
| 72° C. | 30 s | |
| 72° C. | 5 min | |
| 4° C. | ∞ | |

2. Amplification of Library Sequences

A 96-well plate coated with streptavidin was purchased from Thermo Fisher Company, and 100 W of 1 µM 5'-end biotin-modified primer GCCATGTCGTTCTGTGAGC-CAAGG (SEQ ID NO: 5) was incubated in one of the wells at room temperature for 30 minutes, the reaction liquid was discarded, 6 ng of the library constructed in Section 1 above and 20 µl of the DNB preparation buffer I in the BGISEQ-500 kit (made by MGI) were added, primer hybridization with the above biotin-modified primer was performed at 60° C. for 5 minutes, 40 µl of the DNB polymerase I in the BGISEQ-500 sequencing kit (made by MGI) and 4 µl of DNB polymerase II were added, reaction was performed at 30° C. for 60 minutes, after being heated to 65° C., the reaction was terminated, and the reaction solution was carefully discarded. 100 µl of 5 µM sequencing primer GCTCACAGAACGACATGGCTACGATCCGACTT (SEQ ID NO: 6) was added, hybridization was performed at room temperature for 30 minutes, and the reaction solution was carefully discarded;

3. Sequencing (1) Four dNTPs as shown below were synthesized by Acme Bioscience as outsourcing company:

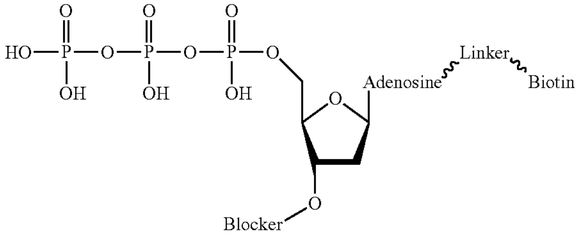

dATP-Linker-biotin

-continued

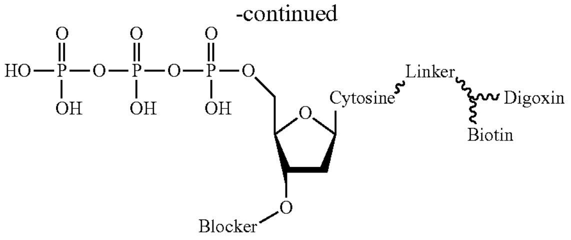

dCTP-Linker-biotin-digoxin

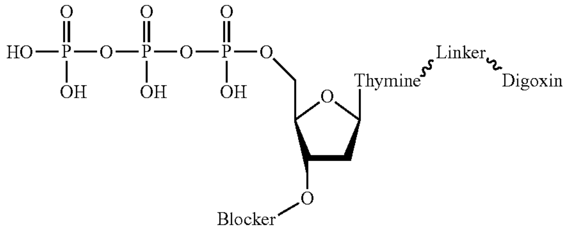

dTTP-Linker-digoxin

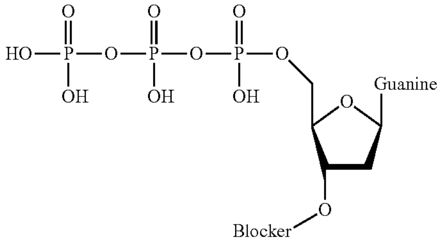

dGTP (2) Preparation of two luciferases:

a. SA-Gluc (purchased from adivity company)

b. Antibody (purchased from Abcam) conjugated with Nluc (purchased from avidity) to prepare Ab-Nluc protein coupling kit was purchased from Thermo, and the conjugation of antibody and Nluc was performed according to the instructions and the procedure as shown in FIG. 1.

(3) Preparation of reagents:

Preparation of other reagents needed in the sequencing reaction Polymerization reaction solution: 50 mM Tris-Hcl, 50 mM NaCl, 10 mM $(NH_4)_2SO_4$, 0.02 mg/ml polymerase BG9 (BGI), 3 mM $MgSO_4$, 1 mM EDTA, 1 µM each of the above four dNTPs Elution buffer: 5×SSC, 0.05% of Tween-20;

Enzyme binding reaction solution: the above two enzymes were diluted into TBST buffer, and the final concentration of each of the two enzymes was 2 µg/ml;

Substrate 1 reaction solution: 50 mM tris-Hcl 0.5 mM Nacl buffer was prepared, and 50× Coelenterazine (nanolight) was diluted to 1×;

Substrate 2 reaction solution: 50 mM tris-Hcl 0.5 mM Nacl buffer was prepared, and 50× NLuc FLASH Substrate (nanolight) was diluted to 1×;

Resection buffer: 20 mM THPP, 0.5 M NaCl, 50 mM Tris-HCl, pH 9.0, 0.05% tween-20;

(4) Sequencing reaction:

Sequencing process:

a. Polymerization: 100 µl of polymerase reaction solution was added to each well of the amplified library, the temperature of a microplate reader was elevated to 55° C., and reaction was performed for 3 minutes so that the four dNTPs were polymerized onto the amplified library. After the reaction solution was carefully discarded, 100 μl of elution reaction solution was added, gently pipetted for several times to remove the elution reaction solution;

b. Ligation of luciferase: 100 μl of enzyme binding reaction solution was added, incubated at 35° C. for 30 minutes, so that SA-gluc ligated to the biotin-labeled dCTP and dATP derivatives, and Ab-Nluc ligated to the digoxin-labeled dCTP and dTTP derivatives, the reaction solution was discarded, the elution solution was added and gently pipetted for several times to remove the elution solution;

c. Enzyme 1 signal detection: appropriate microplate reader parameters were set, the substrate 1 reaction solution was added, Enzyme 1 signal detection was performed, and the highest signal value was recorded;

d. Enzyme 2 signal detection: the substrate reaction solution 1 was removed, appropriate microplate reader parameters were set, the substrate 2 reaction solution was added, Enzyme 2 signal detection was performed, and the highest signal value was recorded;

e. Excision; the substrate 2 reaction solution was removed, 200 μl of elution buffer was added, after being gently pipetted for several times, the elution buffer was discarded, 100 μl of excision reaction solution was added, reaction was performed at 55° C. for 3 minutes, the excision reaction solution was discarded; 200 μl of elution buffer was added for washing, and the washing was repeated for three times;

f. Steps a-e were repeated for the next cycle of sequencing; and a total of 10 bp sequencing was performed.

(5) Sequencing results a. Signal values of the two luminescences were as follows:

| | Substrate 1 signal (W) | Substrate 2 signal (W) |
|---|---|---|
| cycle 1 | 0.1 | 210 |
| cycle 2 | 188 | 0.12 |
| cycle 3 | 173 | 169 |
| cycle 4 | 206 | 0.11 |
| cycle 5 | 198 | 0.13 |
| cycle 6 | 176 | 171 |
| cycle 7 | 0.13 | 186 |
| cycle 8 | 203 | 0.15 |
| cycle 9 | 166 | 159 |
| cycle 10 | 0.12 | 0.16 |

b. Analysis of sequencing results:

According to the luminescence signal values, cycle1 and cycle7 only had signals when substrate 2 is introduced, so that it could be concluded that biotin-dTTP was polymerized in these two cycles, and the first and seventh bases of the library to be tested were T base;

For cycle2, cycle4, cycle5 and cycle8, signals were observed only when substrate 1 was introduced, so that it could be concluded that digoxin-dATP was polymerized in these four cycles, and the second, fourth, fifth and eighth bases of the library to be tested were A base;

For cycle3, cycle6 and cycle9, signals were observed when substrate 1 and substrate 2 were introduced, so that it could be concluded that biotin-digoxin-dCTP was polymerized in these three cycles, and the third, sixth and ninth bases of the library to be tested were C base;

For cycle10, luminescence was not observed when the two substrates were introduced, so that it could be concluded that coldG was polymerized in this cycle, and the tenth base of the library was G base.

In summary, the first 10 bases of the sequence to be tested were: TACAACTACG (SEQ ID NO: 7), which matched 100% with the first 10 bp base sequence TACAACTACG (SEQ ID NO: 7) of the library to be tested.

Example 2

The construction of sequencing library and the amplification of library sequence were the same as shown in Example 1.

Sequencing:

(1) Four dNTPs: as Shown in Example 1

(2) Preparation of luciferases and related proteins a. SA-Gluc (purchased from adivity company)

b. Antibody (purchased from Abcam), and according to the instructions of thermo fisher NHS-s-s-biotin, the antibody was labeled with biotin label to obtain antibody-s-s-biotin.

(3) Preparation of reagents

Preparation of other reagents needed in the sequencing reaction

Polymerization reaction solution: 50 mM Tris-Hcl, 50 mM NaCl, 10 mM $(NH_4)_2SO_4$, 0.02 mg/ml polymerase BG9 (BGI), 3 mM $MgSO_4$, 1 mM EDTA, 1 μM each of the above four dNTPs Elution buffer: 5×SSC, 0.05% of Tween-20;

Enzyme binding reaction solution: the above two proteins SA-Gluc and antibody-s-s-biotin were diluted into TBST buffer, respectively, and the final concentration of each of the two proteins was 2 μg/ml;

Substrate reaction solution: 50 mM Tris-HCl 0.5 mM NaCl buffer was prepared, and 50× Coelenterazine (nanolight) was diluted to 1×;

Enzyme inactivation buffer: 5 mM DTT, 50 mM Tris-HCl, pH 9.0;

Excision buffer: 20 mM THPP, 50 mM Tris-HCl, pH 9.0, 0.5M NaCl, 0.05% Tween-20;

(4) Sequencing reaction a. Polymerization: 100 μl of polymerase reaction solution was added to each well of the amplified library, the temperature of a microplate reader was elevated to 55° C., reaction was performed for 3 minutes to polymerize the four dNTPs onto the amplified library, the reaction solution was carefully removed, 100 μl of the elution reaction solution was added and gently pipetted for several times, and the elution reaction solution was removed;

b. Ligation of luciferase: 100 μl of luciferase SA-Gluc binding reaction solution was added, incubated for 30 min at 35° C., so that SA-gluc was ligated to the biotin-labeled dCTP and dATP derivatives, the reaction solution was removed, the elution solution was added and gently pipetted for several times, and the elution solution was removed;

c. First signal detection: appropriate microplate reader parameters were set, the substrate reaction solution was added, signal detection was performed, and the highest signal value was recorded;

d. Inactivation of enzyme: the substrate reaction solution was removed, the enzyme inactivation buffer was added and incubated at 35° C. for 10 minutes, the reaction solution was removed, and then the elution buffer was added for elution;

e. Second ligation of luciferase: antibody-S—S-biotin reaction solution was added and incubated at 35° C. for 30 minutes, so that antibody-s-s-biotin was ligated to digoxin-labeled dCTP and dTTP derivatives, the reaction solution was removed, the elution buffer was added and pipetted gently for several times, the elution solution was removed, 100 μl of SA-Gluc binding reaction solution was added and incubated at 35° C. for 30 minutes, after the reaction solution was removed, the elution buffer was added, after the elution was completed, the elution buffer was removed;

f. Second signal detection: appropriate microplate reader parameters were set, the substrate reaction solution was added, signal detection was performed, and the highest signal value was recorded;

g. Excision: the substrate 2 reaction solution was removed, 200 μl of the elution buffer was added and gently pipetted for several times, the elution buffer was removed, 100 μl of excision reaction solution was added, reaction was performed at 55° C. for 3 minutes, the excision reaction solution was removed; 200 μl of the elution buffer was added for washing, the washing was repeated for three times;

h. Steps a to g were repeated for the next cycle of sequencing; and a total of 10 bp sequencing was performed.

(5) Sequencing results a. Results of 10 bp signal detection were as follows:

| | First detection (W) | Second detection (W) |
|---|---|---|
| cycle 1 | 0.6 | 223 |
| cycle 2 | 312 | 0.7 |
| cycle 3 | 278 | 327 |
| cycle 4 | 254 | 0.3 |
| cycle 5 | 239 | 0.4 |
| cycle 6 | 243 | 275 |
| cycle 7 | 0.27 | 228 |
| cycle 8 | 267 | 0.5 |
| cycle 9 | 263 | 279 |
| cycle 10 | 0.7 | 0.6 |

b. Analysis of sequencing results:

For cycle1 and cycle7, signal values were obtained only in the second detection, so that it could be concluded that biotin-dTTP was polymerized in these two cycles, and thus the first and seventh bases of the library to be tested were T;

For cycle2, cycle4, cycle5 and cycle8, signals were observed only in the first detection, so that it could be concluded that digoxin-dATP was polymerized in these four cycles, and thus the second, fourth, fifth and eighth bases of the library to be tested were A base;

For cycle3, cycle6 and cycle9, signals were generated in both of the first detection and the second detection, so that it could be concluded that biotin-digoxin-dCTP was polymerized in these two cycles, and thus the third, sixth and ninth of the library to be tested were C base;

For cycle10, light was not emitted in the two signal detections, so that it could be concluded that coldG wsa polymerized in this cycle, and thus the tenth base of this library was G base.

In summary, the first 10 bases of the sequence to be tested were: TACAACTACG (SEQ ID NO: 7), which matched 100% with the first 10 bp base sequence TACAACTACG (SEQ ID NO: 7) of the library to be tested.

What is claimed is:

1. A method for sequencing a nucleic acid molecule, which comprises the following steps:

(1) providing a nucleic acid molecule to be sequenced that is linked to a support, or linking a nucleic acid molecule to be sequenced to a support;

(2) adding a primer for initiating a nucleotide polymerization reaction, a polymerase for performing the nucleotide polymerization reaction, and four compounds to form a reaction system containing a solution phase and a solid phase; wherein, the four compounds are respectively derivatives of nucleotides A, T/U, C and G, and have the ability of base complementary pairing; and, the hydroxyl at the 3'-position of ribose or deoxyribose of the four compounds is protected by a protecting group; and, the first compound is linked with a first molecular label, the second compound is linked with a second molecular label, the third compound is linked with a first molecular label and a second molecular label, or a part of the third compound is linked with a first molecular label and another part of the third compound is linked with a second molecular label, the fourth compound is not linked with any molecular label, wherein the first molecular label and the second molecular label are different;

(3) annealing the primer to the nucleic acid molecule to be sequenced, and forming a duplex linked to the support by using the primer as an initial growing nucleic acid chain together with the nucleic acid molecule to be sequenced;

(4) using the polymerase to carry out the nucleotide polymerization reaction under a condition that allows the polymerase to carry out the nucleotide polymerization reaction, thereby incorporating one of the four compounds into the 3'-end of the growing nucleic acid chain;

(5) allowing the duplex of the previous step to contact with two different luciferases and perform a binding reaction, wherein the two different luciferases can specifically bind to the first molecular label and the second molecular label, respectively, wherein the duplex is contacted with the two different luciferases in a one-step reaction and undergoes a binding reaction; then, allowing the luciferase to undergo a luminescence reaction in the presence of a substrate, and detecting an emitted luminescence signal; and (6) removing the molecular label of each nucleotide.

2. The method according to claim 1, which comprises the following steps:

(1) providing a nucleic acid molecule to be sequenced that is linked to a support, or linking a nucleic acid molecule to be sequenced to a support;

(2) adding a primer for initiating a nucleotide polymerization reaction, a polymerase for performing the nucleotide polymerization reaction, and four compounds to form a reaction system containing a solution phase and a solid phase; wherein, the four compounds are respectively derivatives of nucleotides A, T/U, C and G, and have the ability of base complementary pairing; and, the hydroxyl at the 3'-position of ribose or deoxyribose of the four compounds is protected by a protecting group; and, the first compound is linked with a first molecular label, the second compound is linked with a second molecular label, the third compound is linked with a first molecular label and a second molecular label, or a part of the third compound is linked with a first molecular label and another part of the third compound is linked with a second molecular label, the fourth compound is not linked with any molecular label;

(3) annealing the primer to the nucleic acid molecule to be sequenced, and forming a duplex linked to the support by using the primer as an initial growing nucleic acid chain together with the nucleic acid molecule to be sequenced;

(4) using the polymerase to carry out the nucleotide polymerization reaction under a condition that allows the polymerase to carry out the nucleotide polymerization reaction, thereby incorporating one of the four compounds into the 3'-end of the growing nucleic acid chain;

(5) removing the solution phase of the reaction system in the previous step, keeping the duplex linked to the support, and adding two different luciferases to carry out the binding reaction, wherein the two different luciferases can specifically bind to the first molecular label and the second molecular label, respectively;

(6) removing unbound luciferase by using an elution buffer;

(7) adding a substrate of the first luciferase and detecting luminescence signal at the same time;

(8) removing the solution of the previous step reaction;

(9) adding a substrate of the second luciferase and detecting luminescence signal at the same time;

(10) removing the solution of the previous step reaction; and

(11) removing the molecular label and 3'-protecting group of each nucleotide.

3. The method according to claim 2, wherein the first luciferase and the second luciferase are different.

4. The method according to claim 1, wherein the first molecular label and the second molecular label are selected from the group consisting of biotin, digoxigenin, N3G or FITC, and the first luciferase and the second luciferase are respectively labeled with streptavidin, digoxigenin antibody, N3G antibody or FITC antibody.

5. A kit for sequencing a polynucleotide, which comprises:

(a) four compounds, the four compounds are respectively derivatives of nucleotides A, T/U, C and G, and have the ability of base complementary pairing; and, the hydroxyl at the 3'-position of ribose or deoxyribose of the four compounds is protected by a protecting group; and, the first compound is linked with a first molecular label, the second compound is linked with a second molecular label, the third compound is linked with a first molecular label and a second molecular label, or a part of the third compound is linked with a first molecular label and another part of the third compound is linked with a second molecular label, the fourth compound is not linked with any molecular label; and (b) two different luciferases, the two luciferases can specifically bind to the first molecular label and the second molecular label, respectively;

wherein the first molecular label and the second molecular label are different.

6. The kit according to claim 5, wherein the first molecular label and the second molecular label are selected from the group consisting of biotin, digoxigenin, N3G or FITC, and the first luciferase and the second luciferase are respectively labeled with streptavidin, digoxigenin antibody, N3G antibody or FITC antibody.

7. The kit according to claim 5, further comprising: a reagent and/or device for extracting a nucleic acid molecule from a sample; a reagent for pretreating the nucleic acid molecule; a support for linking the nucleic acid molecule to be sequenced; a reagent for linking the nucleic acid molecule to be sequenced to the support; a primer for initiating a nucleotide polymerization reaction; a polymerase for performing the nucleotide polymerization reaction; one or more buffer solutions; one or more washing solutions; or any combination thereof.

8. The method according to claim 1, further comprises the following step:

(7) repeating steps (3) to (6) or (3) to (5) one or more times to obtain sequence information of the nucleic acid molecule.

9. The method according to claim 2, further comprises the following step:

(12) removing the solution of the previous step reaction.

10. The method according to claim 9, further comprises the following step:

(13) repeating steps (3) to (12) or (3) to (9) one or more times to obtain sequence information of the nucleic acid molecule.

11. The kit according to claim 7, wherein the reagent is a reagent for covalently or non-covalently linking the nucleic acid molecule to be sequenced to the support.

12. The method according to claim 1, wherein the four compounds are shown in the following Formula I, Formula II, Formula III and Formula IV:

Formula I

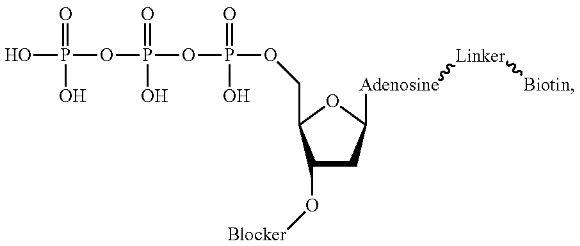

Formula II

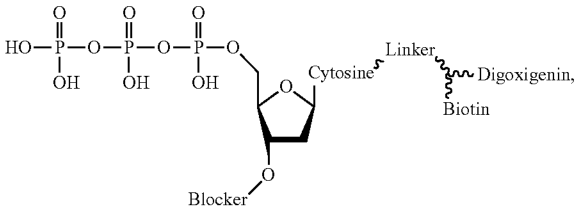

Formula III

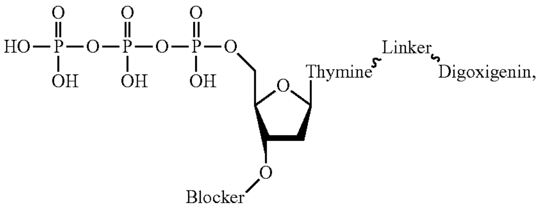

and

Formula IV

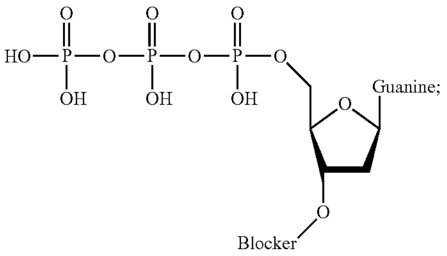

wherein, the Blocker is a 3'-OH protecting group, and the Linker is a linking group.

13. The kit according to claim 5, wherein the four compounds are shown in the following Formula I, Formula II, Formula III and Formula IV:

Formula I

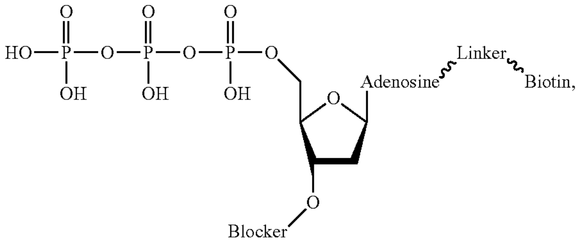

Formula II

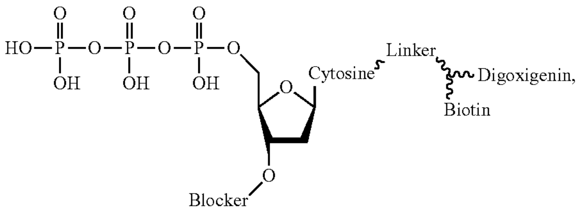

Formula III

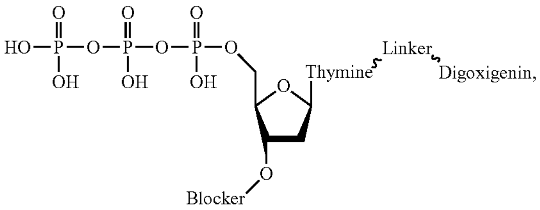

and

Formula IV

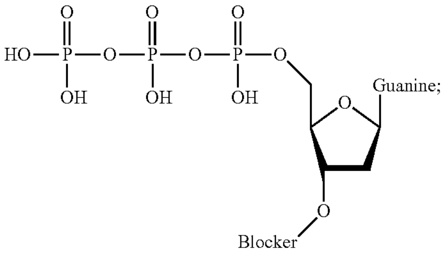

wherein, the Blocker is a 3'-OH protecting group, and the Linker is a linking group.

* * * * *

SEQUENCE LISTING

```
<160> NUMBER OF SEQ ID NOS: 7

<210> SEQ ID NO 1
<211> LENGTH: 233
<212> TYPE: DNA
<213> ORGANISM: Artificial Sequence
<220> FEATURE:
<223> OTHER INFORMATION: DNA sequence  designed

<400> SEQUENCE: 1

gatatctgca ggcatagaat gaatattatt gaatcaataa ttaaagtcgg aggccaagcg      60

gtcttaggaa gacaacaact ccttggctca cagaacgaca tggctacgat ccgactttac     120

aactacgata atgggctgga tacatggaat gattatagat atattaagga ataatgttaa     180

ttaatgccta aattaattaa tctaaggggg ttaatacttc agcctgtgat atc            233


<210> SEQ ID NO 2
<211> LENGTH: 15
<212> TYPE: DNA
<213> ORGANISM: Artificial Sequence
<220> FEATURE:
<223> OTHER INFORMATION: primer

<400> SEQUENCE: 2

gatatctgca ggcat                                                       15


<210> SEQ ID NO 3
<211> LENGTH: 15
```

-continued

```
<212> TYPE: DNA
<213> ORGANISM: Artificial Sequence
<220> FEATURE:
<223> OTHER INFORMATION: primer

<400> SEQUENCE: 3

gatatcacag gctga                                                   15


<210> SEQ ID NO 4
<211> LENGTH: 30
<212> TYPE: DNA
<213> ORGANISM: Artificial Sequence
<220> FEATURE:
<223> OTHER INFORMATION: split oligo

<400> SEQUENCE: 4

atgcctgcag atatcgatat cacaggctga                                   30


<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5

gccatgtcgt tctgtgagcc aagg                                         24


<210> SEQ ID NO 6
<211> LENGTH: 32
<212> TYPE: DNA
<213> ORGANISM: Artificial Sequence
<220> FEATURE:
<223> OTHER INFORMATION: primer

<400> SEQUENCE: 6

gctcacagaa cgacatggct acgatccgac tt                                32


<210> SEQ ID NO 7
<211> LENGTH: 10
<212> TYPE: DNA
<213> ORGANISM: Artificial Sequence
<220> FEATURE:
<223> OTHER INFORMATION: the first 10bp base sequence

<400> SEQUENCE: 7

tacaactacg                                                         10
```